(12) United States Patent
Duchene et al.

(10) Patent No.: US 6,255,487 B1
(45) Date of Patent: Jul. 3, 2001

(54) PROCESS OF PREPARING [2-(1-PIPERAZINYL)ETHOXY]METHYL COMPOUNDS

(75) Inventors: Guy Duchene, Sterrebeek; Michel Deleers, Linkebeek; Guy Bodson, Bellefontaine; Genevieve Motte, Chastre; Francoise Lurquin, Villers-la-Ville, all of (BE)

(73) Assignee: UCB, S.A., Brussels (BE)

( * ) Notice: Subject to any disclaimer, the term of this patent is extended or adjusted under 35 U.S.C. 154(b) by 0 days.

(21) Appl. No.: 09/532,159

(22) Filed: Mar. 21, 2000

Related U.S. Application Data

(62) Division of application No. 09/155,977, filed as application No. PCT/BE97/00038 on Mar. 28, 1997, now Pat. No. 6,140,501.

(30) Foreign Application Priority Data

Apr. 10, 1996 (BE) .................................... 9600310

(51) Int. Cl.⁷ ........................ C07D 295/10; C07D 295/14
(52) U.S. Cl. .............................................. 544/396
(58) Field of Search ............................... 544/396

(56) References Cited

U.S. PATENT DOCUMENTS 4,525,358  6/1985  Baltes et al. .................... 514/255

FOREIGN PATENT DOCUMENTS

| 1 174 819 | 12/1969 | (GB) . |
| 1 184 395 | 3/1970  | (GB) . |
| 2 225 320 | 5/1990  | (GB) . |
| 2 225 321 | 5/1990  | (GB) . |

OTHER PUBLICATIONS

Jilek, Jiri; Holubek, Jiri; Svatek, Emil; Metys, Jan; Frycova, Hana Pomykacek, Josef; Protiva, Miroslav, Collect. Czech. Chem. Commun. (1988), 53(4), 870–83.*

John D. Roberts and Marjorie C. Caserio, "Basic Principles of Organic Chemistry", Benjamin, New York, 1964, p 257–259.*

Ohtaka, Hiroshi; Kanazawa, Toshiro; Ito, Keizo; Tsukamoto, G., Chem. Pharm. Bull. (1987), 35(8), 3270–5.*

* cited by examiner

Primary Examiner—Richard L. Raymond
Assistant Examiner—Thomas McKenzie
(74) Attorney, Agent, or Firm—Wenderoth, Lind & Ponack, L.L.P.

(57) ABSTRACT

The present invention relates to novel substituted [2-(1-piperazinyl)-ethoxy]methyl compounds of formula (I)

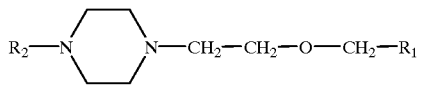

in which $R_1$ represents a —$CONH_2$, —CN, —COOH, —COOM or —$COOR_3$ group, M being an alkali metal and $R_3$ being an alkyl radical having from 1 to 4 carbon atoms; and $R_2$ represents a hydrogen atom or a group —$COR_4$ or —$R_5$, where $R_4$ is chosen from the groups —$OR_6$ or —$R_7$, in which $R_5$ represents an alkyl or alkylaryl radical, $R_6$ represents a linear or branched alkyl radical having from 1 to 4 carbon atoms, a haloalkyl, alkylaryl, alkylnitroaryl or alkylhaloaryl radical, and $R_7$ represents a haloalkyl radical, to a process for the preparation of these compounds, and to their use for the preparation of compounds which are themselves valuable intermediates for the preparation of 2-[2-[4[(4-chlorophenyl)phenylmethyl]-1-piperazinyl]ethoxy]-acetic acid or 2-[2-[4-[bix(4-fluorophenyl)methyl]-1-piperazinyl]ethoxy]-acetic acid and/or pharmaceutically acceptable salts thereof.

4 Claims, No Drawings

PROCESS OF PREPARING [2-(1-PIPERAZINYL)ETHOXY]METHYL COMPOUNDS

This application is a division of Ser. No. 09/155,977 filed Oct. 9, 1998, now U.S. Pat. No. 6,140,501, which is a 371 of PCT/BE97/00038 filed Mar. 28, 1997.

The present invention relates to novel compounds, substituted [2-(1-piperazinyl)ethoxy]methyl compounds of formula

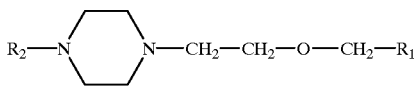

(I)

in which $R_1$ represents a —$CONH_2$, —CN, —COOH, —COOM or —$COOR_3$ group, M being an alkali metal and $R_3$ being an alkyl radical having from 1 to 4 carbon atoms; and $R_2$ represents a hydrogen atom or a group —$COR_4$ or —$R_5$, where $R_4$ is chosen from the groups —$OR_6$ or —$R_7$, in which $R_5$ represents an allyl or alkylaryl radical, $R_6$ represents a linear or branched alkyl radical having from 1 to 4 carbon atoms, a haloalkyl, alkylaryl, alkylnitroaryl or alkylhaloaryl radical, and $R_7$ represents a haloalkyl radical, to a process for the preparation of these compounds, and to their use for the preparation of compounds of formula

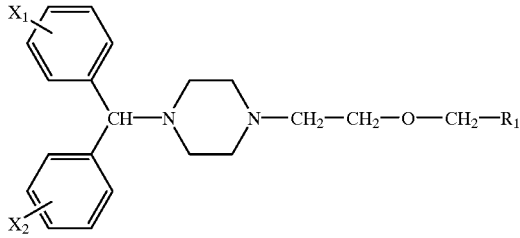

(II)

in which $R_1$ has the same meaning as in formula I and $X_1$ and $X_2$ independently represent a hydrogen, fluorine, chlorine or bromine atom. In the case where $R_1$ represetns a —COOH group and where $X_1$ represents a chlorine atom in position 4 and $X_2$ represents a hydrogen atom, the compound of formula II is 2-[2-[4-[(4-chlorophenyl)phenylmethyl]-1-piperazinyl]ethoxy]acetic acid of formula

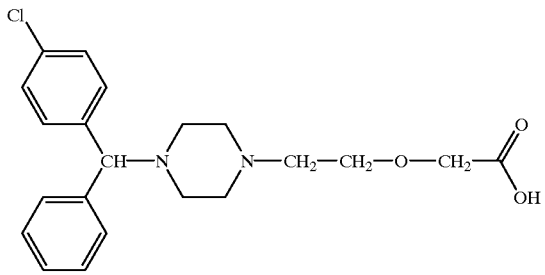

(III)

In the case where $R_1$ represents a —$CONH_2$, —CN, —COOM or —$COOR_3$ group, M being an alkali metal and $R_3$ being an alkyl radical having from 1 to 4 carbon atoms and where $X_1$ represents a chlorine atom in position 4 and $X_2$ a hydrogen atom, the compounds of formula II are valuable intermediates for the preparation of 2-[2-[4-[(4-chlorophenyl)phenylmethyl]-1-piperazinyl]ethoxy]acetic acid of formula III, as well as pharmaceutically acceptable salts thereof. 2-[2-[4-[(4-Chlorophenyl)phenylmethyl]-1-piperazinyl]ethoxy]acetic acid dihydrochloride, a product which is also known under the common international name of cetrizine, is described in U.S. Pat. No. 4,525,358 and has been introduced as a medicament for the treatment of allergic syndromes, for instance chronic and acute allergic rhinitis, allergic conjunctivitis, pruritus, urticaria, etc. In its therapeutic application, this product proved to be remarkably free of side effects on the central nervous system, such as drowsiness, attenuated mental performance, etc. (cfr. D. P. TASHKIN et. al., Annals of Allergy, Part II, 59, (1987), 49–52, as well as F. M. GENGO et al., Annals of Allergy, Part II, 59, (1987), 53–57). In the case where $R_1$ represents a —COOH group and where $X_1$ and $X_2$ each represent a fluorine atom in position 4, the compound of formula II is 2-[2-[4-[bis(4-fluorophenyl)methyl]-1-piperazinyl]ethoxy] acetic acid of formula

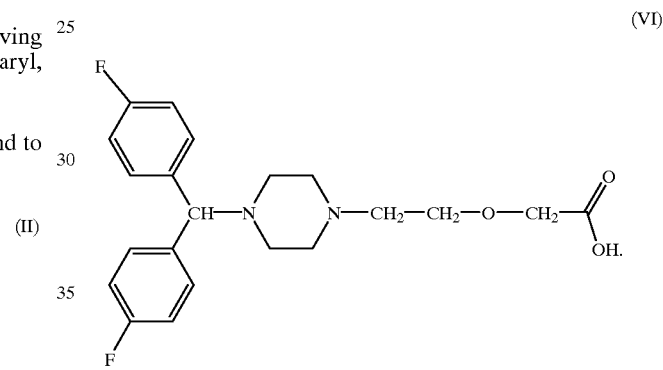

(VI)

In the case where $R_1$ represents a —$CONH_2$, —CN, —COOM or —$COOR_3$ group, M being an alkali metal and $R_3$ being an alkyl radical having from 1 to 4 carbon atoms and where $X_1$ and $X_2$ each represent a fluorine atom in position 4, the compounds of formula II are valuable intermediates for the preparation of 2-[2-[4-[bis(4-fluorophenyl)methyl]-1-piperazinyl]ethoxy]acetic acid of formula IV as well as pharmaceutically acceptable salts. 2-[2-[4-[Bis(4-fluorophenyl)methyl]-1-piperazinyl]ethoxy]acetic acid dihydrochloride is also known under the common international name of efletrizine. The use of efletirizine for the treatment of rhinitis or rhino-conjunctivitis of allergic origin has been suggested in several recent communications (51$^{st}$ Annual Meeting or American Academy of Allergy and Immunology, reproduced in J. Allergy Clin. Immunol., 95/1 (1995), part 2, Abstract 229 and XV$^{th}$ Congress of Allergology and Clinical Immunology, reproduced in Allergy & Clin. Immunol. News, (1994) suppl. No. 2, abstracts 428, 1136, 1496 and 1864). These communications indicate that the intranasal administration of efletirizine might provide an effective therapeutic treatment of rhinitis or rhino-conjunctivitis of allergic origin. U.S. Pat. No. 4,525,358 in the name of the Applicant, describes the synthesis of 2-[2-[4-[(4-chlorophenyl)phenylmethyl)-1-piperazinyl]ethoxy] acetic acid and its dihydrochloride. In this synthesis, the starting material is 1-[(4-chlorophenyl)phenylmethyl] piperazine, which may be reacted with methyl (2-chloroethoxy)acetate or 2-(2-chloroethoxy)acetamide to form respectively methyl 2-[2-[4-[(4-chlorophenyl) phenylmethyl]-1-piperazinyl]ethoxy]acetate (compound of formula II which $R_1$=—$COOH_3$, $X_1$=—Cl (position 4) and $X_2$=—H) or 2-[2-[4-[(4-chlorophenyl)phenylmethyl]-1-piperazinyl]ethoxy]acetamide (compound of formula II with $R_1$=—$CONH_2$, $X_1$=—Cl (position 4) and $X_2$=—H). This methyl ester as well as this acetamide may then be subjected to hydrolysis with an inorganic base (potassium or sodium hydroxide) to form the sodium or potassium salt, which is readily converted into cetirizine and its dihydrochloride.

British Patent application 2,225,320, also in the name of the Applicant, gives an alternative synthetic route for the preparation of 2-[2-[4-[(4-chlorophenyl)phenylmethyl]-1-piperazinyl]ethoxy]acetic acid and its dihydrochloride.

According to that patent, 2-[2-[4-[(4-chlorophenyl) phenylmethyl]-1-piperazinyl]ethoxy]acetic acid and its dihydrochloride are prepared by a process which is characterized in that 2-[4-[(4-chlorophenyl)phenylmethyl]-1-piperazinyl]ethanol is reacted with an alkali metal haloacetate, in the presence of an alkali metal alkoxide, and in that the alkali metal salt thus obtained is converted into the corresponding acid and, where appropriate, into its dihydrochloride.

British Patent Application 2,225,321, also in the name of the Applicant provides another synthetic process which makes it possible to prepare 2-[2-[4-[(4-chlorophenyl) phenylmethyl]-1-piperazinyl]ethoxy]acetic acid and its dihydrochloride.

According to that patent, 2-[2-[4-[(4-chlorophenyl) phenylmethyl]-1-piperazinyl]ethoxy]acetic acid and its dihydrochloride are prepared by a process which is characterized in that 2-[2-[4-[(4-chlorophenyl)phenylmethyl]-1-piperazinyl]ethoxy]acetonitrile (compound of formula II with $R_1$=—CN, $X_1$=—Cl (position 4) and $X_2$=—H) is hydrolysed in aqueous, alcoholic or aqueous-alcoholic medium and with a base or with an acid, and in that the acid thus obtained is converted, where appropriate, into its dihydrochloride.

The 2-[2-[4-[(4-chlorophenyl)phenylmethyl]-1-piperazinyl]ethoxy]acetonitrile used as starting material is obtained by reacting 1-[(4-chlorophenyl)phenylmethyl] piperazine with a 2-haloethoxyacetonitrile. This reaction is carried out in the presence of an acid acceptor, such as an alkali metal carbonate, and optionally in the presence of a small amount of alkali metal iodide to accelerate the reaction, in an inert organic solvent such as an alcohol (for example n-butanol, etc.), preferably at a temperature in the region of the reflux temperature.

Given the increasing therapeutic value of cetirizine and of compounds of similar structure, the Applicant set itself the objective and undertook research studies with the aim of developing a new synthetic route to 2-[2-[4-[( 4-chlorophenyl)phenylmethyl]-1-piperazinyl]ethoxy]acetic acid and pharmaceutically acceptable salts thereof which would make it possibe to obtain this compound from known and/or readily accessible reagents and which would moreover provide this compound in a sufficient purity and an economically acceptable yield. Moreover, for the puprose of simplifying the industrialization of the process, the Applicant set itself the further objective of developing a synthetic route which might have fewer steps than the known processes.

In addition, given the therapeutic value of other compounds of formula II, such as efletirizine for example, it would be advantageous for these other compounds to be able to be prepared according to essentially similar processes.

Consequently, it is necessary to find precursors which, on the one hand, may themselves be prepared readily and economically, and, on the other hand, may be converted readily and in high yields into compounds of formula II. The Applicant has just discovered a family of compounds, namely substituted [2-(1-piperazinyl)ethoxy]methyl compounds which satisfy this objective entirely.

The subject of the present invention is thus, as novel compounds, substituted [2-(1-piperazinyl)ethoxy]methyl compounds of formula

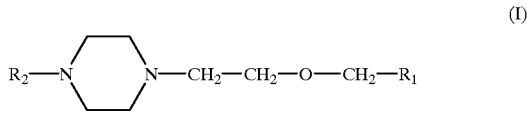

(I)

in which $R_1$ represents a —$CONH_2$, —CN, —COOH, —COOM or —$COOR_3$ group, M being an alkali metal and $R_3$ being an alkyl radical having from 1 to 4 carbon atoms; and $R_2$ represents a hydrogen atom or a group —$COR_4$ or —$R_5$, where $R_4$ is chosen from the groups —$OR_6$ or —$R_7$, in which $R_5$ represents an allyl or alkylaryl radical, $R_6$ represents a linear or branched alkyl radical having from 1 to 4 carbon atoms, a haloalkyl, alkylaryl, alkylnitroaryl or alkylhaloaryl radical, and $R_7$ represents a haloalkyl radical.

These compounds may readily be obtained by reaction of a piperazine of formula

(V)

in which $R_2$ represents a hydrogen atom or a group —$COR_4$ or —$R_5$, where $R_4$ is chosen from the groups —$OR_6$ or —$R_7$, in which $R_5$ represents an allyl or alkylaryl radical, $R_6$ represents a linear or branched alkyl radical having from 1 to 4 carbon atoms, a haloalkyl, alkylaryl, alkylnitroaryl or alkylhaloaryl radical, and $R_7$ represents a haloalkyl, with a substituted [2-haloethoxy]methyl of formula $$X—CH_2—CH_2—O—CH_2—R_1 \qquad (VI)$$

in which $R_1$ represetns a —$CONH_2$, —CN, —COOH, —COOM or —$COOR_3$ gorup, M being an alkali metal and $R_3$ being an alkyl radical having from 1 to 4 carbon atoms and X represents a halogen atom. Usually, a compound of formula VI is used in which X represents a chlorine or iodine atom, but this reaction may also be carried out with the corresponding bromide. It has been observed that when X represetns an iodine atom, it is advantageous to work at fairly low temperatures (below 40° C.) and for relatively short times (2 hours for example).

This reaction is generally carried out by heating to between 30 and 180° C., for several hours, in a solvent chosen from aliphatic alcohols, aliphatic ketones (for example methy ethyl ketone), aromatic hydrocarbons (for example toluene or xylene) or alternatively in water and, in the presence of an acid acceptor such as a tertiary organic base (for example triethylamine) or an inorganic base (for example sodium carbonate). When a large excess of piperazine (more than three equivalents relative to the [2-haloethoxy]methyl) is used, the piperazine itself acts as acid acceptor and it is not essential to add an additional acid acceptor. Advantageously, a piperazine and its dihydrochloride may also be used in equivalent amounts.

In general, in order to prepare the substituted [2-(1-piperazinyl)-ethoxy]methyl compounds of the invention, it is preferred, for obvious reasons of simplicity, to use the piperazine of formula V in which $R_2$ represents a hydrogen atom. It may nevertheless prove wise to protect one of the amine functions of the piperazine during this reaction with a conventional protecting group for this function in order to prevent the piperazine from reacting twice with the compound of formula VI.

As protecting group for the amine function, any protecting group known to those skilled in the art for this purpose may be used.

To this end, it is possible to choose a protecting group which, after formation of the compound of formula I, may be selectively cleaved off according to the equation:

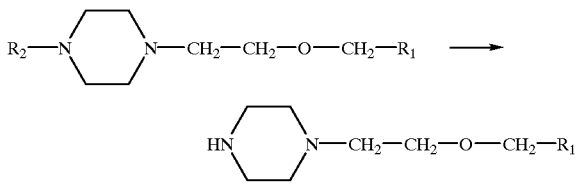

Protecting groups which are particularly suitable in this case are for example haloalkyl, alkylhaloaryl, alkylaryl, alkylnitroaryl, and alkylhaloaryl carbamates, amides such as trifluoroacetamide or alternatively tertiary amines, such as N-allylamines or n-alkylarylamines.

With these groups, the reaction for the deprotection of the amine function of the piperazine may be carried out by a simple heating, by catalytic hydrogenation or by hydrolysis by means of a base or an acid, according to techniques which are well known to those skilled in the art.

According to one variant, as protecting group for the amine function, a group may also be chosen which may be cleaved off under conditions such that, in the case where $R_1$ represents a —$CONH_2$, —CN, —COOM or —$COOR_3$ group, M being an alkali metal and $R_3$ being an alkyl radical having from 1 to 4 carbon atoms, simultaneously with the reaction for deprotection of the amine function, the group $R_1$ is converted into a —COOH group, and, in the case where $R_1$ represents a —COOH group, this —COOH group is conserved during the reaction for deprotection of the amine function.

This reaction is carried out according to the equation:

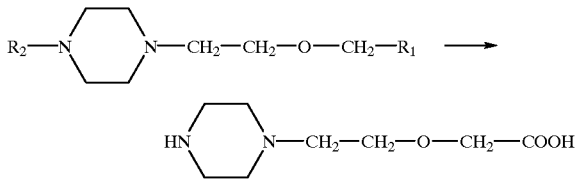

Protecting groups which are particularly suitable in this case are for example alkyl carbamate groups.

With such carboxylated groups, the amine function of the piperazine may be deprotected by heating for several hours in alcoholic or aqueous medium in the presence of an inorganic base or by any other conventional method known to those skilled in the art.

In the two preceding equations, $R_1$ represents a —$CONH_2$, —CN, —COOH, —COOM or —$COOR_3$ group, M being an alkali metal and $R_3$ being an alkyl radical having from 1 to 4 carbon atoms; and $R_2$ represents a hydrogen atom or a group —$COR_4$ or —$R_5$, where $R_4$ is chosen from the groups —$OR_6$ or —$R_7$, in which $R_5$ represents an allyl or alkylaryl radical, $R_6$ represents a linear or branched alkyl radical having from 1 to 4 carbon atoms, a haloalkyl, alkylaryl, alkylnitroaryl or alkylhaloaryl radical, and $R_7$ represents a haloalkyl radical.

The substituted [2-(1-piperazinyl)ethoxy]methyl compounds of formula I thus prepared find their main value as precursors for the preparation of compounds of formula II (or compounds of formulae III and IV in the case where $R_1$ represents a —COOH group) which may thus be prepared in sufficient purity, in an economically acceptable yield, in fewer steps and starting from the same precursors, which represents an appreciable advantage as regards simplifying the industrial process and reducing the production costs.

Consequently, the present invention also relates to the preparation of compounds of formula II (or compounds of formulae III and IV in the case where $R_1$ represents a —COOH group) by reaction of a compound of formula I in which $R_2$ represents a hydrogen atom with a diphenylmethyl halide of formula VII according to the equation:

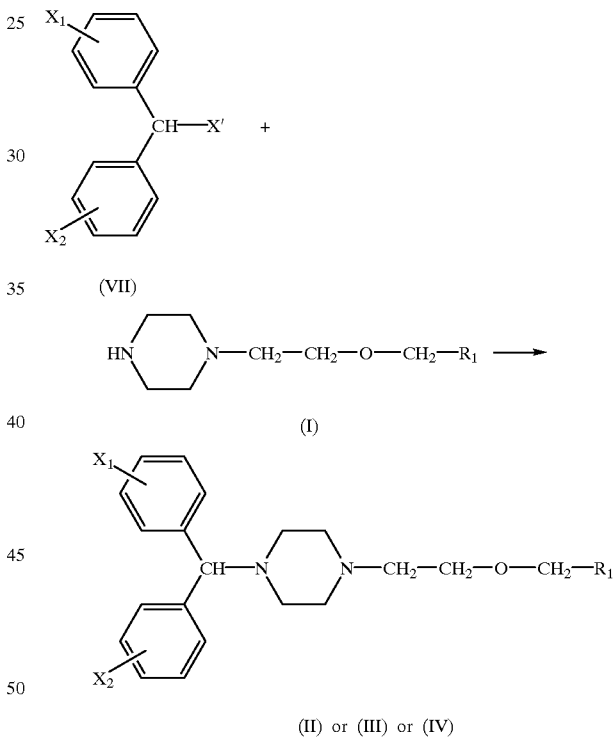

in which $R_1$ represents a —$CONH_2$, —CN, —COOH, —COOM or —$COOR_3$ group, M being an alkali metal and $R_3$ being an alkyl radical having from 1 to 4 carbon atoms; and X' represents a halogen atom chosen from chlorine, bromine and iodine, $X_1$ and $X_2$ independently represent a hydrogen, fluorine, chlorine or bromine atom.

This reaction is carried out by reacting the diphenylmethyl halide of formula VI with the compound of formula I in molar proportions of between 4:1 and 1:4 for a period of between a few minutes and several hours at a temperature between about 60 and about 160° C., in an inert solvent chosen from aliphatic alcohols, aliphatic ketones (for example methyl ethyl ketone), aromatic hydrocarbons (for example toluene or xylene), aliphatic nitriles (for example acetonitrile). It is optionally possible to carry out the reaction in the presence of an acid acceptor such as a tertiary organic base (for example triethylamine) or an inorganic base (for example sodium carbonate). This reaction may optionally be carried out in the presence of an alkali metal iodide.

As indicated above, the compounds of formula II (in which $R_1$ represents a —$CONH_2$, —CN, —COOM or —$COOR_3$ group, M being an alkali metal and $R_3$ being an alkyl radical having from 1 to 4 carbon atoms, $X_1$ represents a chlorine atom in position 4 and $X_2$ a hydrogen atom) are already known and their conversion into 2-[2-[4-[(4-chlorophenyl)phenylmethyl]-1-piperazinyl]ethoxy]acetic acid of formula III has already been described in aqueous, alcoholic or aqueous-alcoholic medium, and with a base or with an acid. Moreover, the compound of formula II in which $R_1$ represents a —COOH group and $X_1$ represents a chlorine atom in position 4 and $X_2$ a hydrogen atom, is 2-[2-[4[(4-chlorophenyl)phenylmethyl]-1-piperazinyl] ethoxy]acetic acid of formula III. Thus, for the subsequent conversion of the alkyl 2-[2-[4-[(4-chlorophenyl)phenylmethyl]-1-piperazinyl]ethoxy]acetate (compound of formula II with $R_1$=—$COOR_3$, $X_1$=—Cl in position 4 and $X_2$=—H) or 2-[2-[4-[(4-chlorophenyl)phenylmethyl]-1-piperazinyl]ethoxy]acetamide (compound of formula II with $R_1$=—$CONH_2$, $X_1$=—Cl in position 4 and $X_2$=—H) into 2-[2-[4-[(4-chlorophenyl)phenylmethyl)-1-piperazinyl] ethoxy]acetic acid of formula III, reference is made to U.S. Pat. No. 4,525,358 and for conversion of the 2-[2-[4-[(4-chlorophenyl)phenylmethyl]-1-piperazinyl]ethoxy] acetonitrile (compound of formula II with $R_1$=—CN, $X_1$=—Cl in position 4 and $X_2$=—H), reference is made to British Patent application 2,225,321.

For the conversion of the other compounds of formula II, the process is performed analogously.

The examples which follow illustrate the invention without however limiting it. In these examples, the melting points were determined by differential scanning calorimetry (D.S.C.) with a temperature gradient of 20° C./min. The mass spectra were recorded with a Finnigan MAT TSQ 700 machine. The nuclear magnetic resonance (NMR) spectra were recorded with a Bruker machine at 250 MHz in dimethyl sulphoxide using tetramethylsilane as internal standard. The chemical shifts are indicated in δ (ppm). The letters s, d, dd, t, q, b and m respectively indicate a singlet, a doublet, a doubled doublet, a triplet, a quartet, abroad peak and multiplet.

EXAMPLES

Example I

Preparation of Substituted [2-(1-piperazinyl)ethoxy] methyl Compounds of Formula I I.1. Preparation of the compounds of formula I with $R_2$=—H.

I.1.1. 2-[2-(1-Piperazinyl)ethoxy]acetamide.

I.1.1.1.

A mixture of 13.15 g of (2-chloroethoxy)acetamide (0.1 mol) and 43 g of anhydrous piperazine (0.5 mol) in 250 ml of toluene is introduced into a round-bottomed flask fitted with a water-cooled condenser and a mechanical stirrer. The mixture is heated at the reflux temperature for 4 hours. The precipitate formed is filtered off while hot and the solvent of the filtrate is evaporated off under reduced pressure to dryness. The evaporation residue is purified by chromatography on silica gel (eluent: 14/5/1 (v/v/v) of dichloromethane/methanol/28% aqueous ammonia solution). 7.4 g of 2-[2-(1-piperazinyl)ethoxy]acetamide are obtained in the form of a yellow oil. Yield: 39% Mass spectrum: 188 ($MH^+$), 99 ($HN(C_4H_8)N^+=CH_2$), 44 ($CONH_2$).

I.1.1.2. (variant).

8.6 g (0.1 mol) of piperazine, 15.9 g (0.1 mol) of piperazine dihydrochloride, 10.8 ml (0.6 mol) of water and 86 ml of methyl ethyl ketone are introduced into a 250 ml three-necked round-bottomed flask fitted with a water-cooled condenser and a mechanical stirrer.

The mixture is brought to a temperature of 65° C. 13.8 g (0.1 mol) of 2-chloroethoxy)acetamide are then added in a single portion. The mixture is maintained at the temperature of 65° C. for 16 hours. The mixture is allowed to cool to room temperature, and the two phases are then left to separate out by settling before separating them. The lower phase (oily phase immiscible with the methyl ethyl ketone) is rinsed with 2×25 ml of methyl ethyl ketone. This oil is taken up in 50 ml of ethanol and is left stirring for 15 minutes. The precipitate formed (piperazine dihydrochloride) is filtered off and the filtrate is concentrated under reduced pressure at 50° C. on a rotary evaporator. 27 g of a yellow oil are obtained which product is purified by preparative chromatography on silica gel (eluent: 82/15/1/2 (v/v/v/v) mixture of dichloromethane/methanol/28% (weight) aqueous ammonia solution/water). 10.7 g of [2-(1-piperazinyl)ethoxy]acetamide are finally obtained in the form of a colorless oil which crystallizes. Yield: 57.1% NMR: δ: 2.33 (4H, m); 2.43 (2H, t, 5.54 Hz); 2.67 (4H, m); 2.79 (1H, bs); 3.53 (2H, t, 5.53 Hz), 3.78 (2H, s); 7.18 (1H, bs); 7.53 (1H, bs). Mass spectrum: 188 ($MH^+$)

I.1.2. 2-(1-Piperazinyl)ethoxyacetonitrile.

8.6 g (0.1 mol) of piperazine, 15.9 g (0.1 mol) of piperazine dihydrochloride, 0.6 ml of water and 40 ml of ethanol are introduced into a 250 ml three-necked round-bottomed flask fitted with a water-cooled condenser and a mechanical stirrer. The mixture is brought to a temperature of 70° C. 11.9 g (0.1 mol) of (2-chloroethoxy)acetonitrile dissolved in 48 ml of ethanol are then added dropwise over 15 minutes. The mixture is maintained at 70° C. for 16 hours. The mixture is allowed to return to room temperature and is then cooled on an ice bath. The precipitate formed is then filtered off. The filtrate is concentrated under reduced pressure on a rotary evaporator and the residue (oil+solid) is taken up in 50 ml of ethanol. The mixture is left stirring for 15 minutes. The precipitate formed (piperazine dihydrochloride) is filtered off and the filtrate is concentrated under vacuum at 50° C. on a rotary evaporator.

The evaporation residue is purified by preparative chromatography on silica gel (eluent: 94.5/5/0.5 (v/v/v) mixture of dichloromethane/methane/28% (by weight) aqueous ammonia solution gradually replaced by an 89/10/1 (v/v/v) mixture of the same constituents). 4.7 g of 2-(1-piperazinyl) ethoxyacetonitrile are thus obtained in the form of an orange-colored oil. Yield: 27.8% NMR: δ: 2.36 (4H, m); 2.47 (2H, t, 5.6 Hz); 2.71 (4H, m); 3.6 (2H, t, 5.6 Hz), 4.44 (2H, s). Mass spectrum: 170 ($MH^+$).

I.1.3. Methyl 2-(1-piperazinyl)ethoxyacetate.

8.6 g (0.1 mol) of piperazine, 17.7 g (0.1 mol) of piperazine dihydrochloride, 10.8 ml (0.6 mol) of water and 40 ml of methanol are introduced into a 250 ml three-necked round-bottomed flask fitted with a water-cooled condenser and a mechanical stirrer. The mixture is brought to a temperature of 39° C. 13.8 g (0.1 mol) of the methyl ester of (2-chloroethoxy)acetic acid dissolved in 17 ml of methanol are then added dropwise over 35 minutes. The mixture is maintained at 65° C. for 48 hours. The mixture is allowed to cool to room temperature and the piperazine salts which have precipitated are filtered off. The filtrate is concentrated under reduced pressure on a rotary evaporator at 50° C. 31.6 g of a yellow oil are obtained, which product is purified by preparative chromatogrpahy on silica gel (eluent: 94.5/5/0.5 (v/v/v) mixture of dichloromethane/methanol/28% (by weight) aqueous ammonia solution gradually replaced by a 73.5/25/2.5 (v/v/v) mixture of the same constitutents). 9.83 g of methyl 2-(1-piperazinyl)ethoxy-acetate are obtained in the form of a colorless oil. Yield: 48.6% NMR: δ: 2.54 (2H, t, 5.6 Hz); 2.60 (4H, m); 2.95 (4H, m); 3.58 (2H, t, 5.6 Hz); 3.65 (3H, s); 4.10 (2H, s). Mass spectrum: 202 ($M^+$)

I.1.4. 2-(1-Piperazinyl)ethoxyacetic acid.

8.6 g (0.1 mol) of piperazine, 17.7 g (0.1 mol) of piperazine dihydrochloride and 50 ml of water are introduced into a 100 ml three-necked round-bottomed flask fitted with a water-cooled condenser and a mechanical stirrer. The mixture is brought to a temperature of 70° C. 15.2 g of (2-chloroethoxy) acetic acid are then added dropwise over 15 minutes. The mixture is brought to a temperature of 80° C. with stirring and is maintained at this temperature for 27 hours. The mixture is allowed to cool to room temperature and the water is evaporated off under reduced pressure on a rotary evaporator. The evaporation residue is taken up in 50 ml of ethanol and maintained at 50° C. with stirring for 45 minutes. It is then placed in an ice bath and is stirred for 1 hour. The precipitate (piperazine dihydrochloride) formed is then filtered off and the solvents are evaporated off under reduced pressure on a rotary evaporator at 50° C. 22.4 g of a yellow oil are obtained. 10 g of this mixture are purified on 130 g of Amberlyte IRA-400 resin. Elution is carried out first with 600 ml of water and then with aqueous 0.5 M ammonium acetate solution. The fractions containing the 2-(1-piperazinyl) ethoxyacetic acid or its salt are combined and the water is removed therefrom under reduced pressure at 60° C. on a rotary evaporator. 18.2 g of a mixture containing white crystals and an oil are recovered. This mixture is taken up in 75 ml of isopropanol and the insoluble crystals are filtered off. The filtrate is acidified with 20 ml of a 9N solution of hydrochloric acid in ethanol. The precipitate formed is filtered off quickly, washed with isopropanol and dried on a rotary evaporator under reduced pressure at 50° C. 7.1 g of a white solid are obtained, which solid is purified by subliming the ammonium chloride salts (4 hours at 135° C. under 0.1 mbar and then 8 hours at 150° C. under 0.1 mbar). 1.4 g of 2-(1-piperazinyl)ethoxyacetic acid dihydrochloride are thus obtained. Yield: 12%. NMR: δ: 2.36 (2H, t, 4.8 Hz); 3.45 (4H, m); 3.53 (4H, m); 3.88 (2H, t, 4.8 Hz); 4.09 (2H, s); 10 (1H, bs). Mass spectrum: 189 ($MH^+$) Elemental analysis:

| Atom | C | H | N |
|---|---|---|---|
| % Calculated | 36.79 | 6.95 | 10.73 |
| % Found | 36.57 | 7.07 | 10.69 |

I.2. Preparation of compounds of formula I with $R_2$=—$CH_2$—$C_6H_5$.

I.2.1. 2-(4-Benzyl-1-piperazinyl)ethoxyacetamide.

I.2.1.1.

8.8 g (0.05 mol) of 1-benzylpiperazine, 7.6 g (0.55 mol) of (2-chloroethoxy)acetamide, 11.7 g (0.11 mol) of sodium carbonate, 0.050 g of potassium iodide and 44 ml of methyl ethyl ketone are introduced into a 100 ml three-necked round-bottomed flask fitted with a water-cooled condenser and a mechanical stirrer. The mixture is brought to the reflux temperature and is maintained at this temperature for 20 hours. The mixture is allowed to cool to room temperature and 50 ml of water are added. The methyl ethyl ketone is then removed under reduced pressure on a rotary evaporator. The aqueous phase is then extracted with 2×50 ml of dichloromethane. The organic phases are combined and are washed with 25 ml of saturated ammonium chloride solution. The solution is dried over sodium sulphate and then filtered and concentrated under reduced pressure using a rotary evaporator. 14.15 g of a brown oil which crystallizes are obtained, and this oil is purified by preparative chromatography on silica gel (eluent: 97/3/0.3 (v/v/v) mixture of dichloromethane/methanol/28% aqueous ammonia). 11.5 g of a yellow solid are obtained. Yield: 82.9%

After recrystallization from ethyl acetate, the 2-(4-benzyl-1-piperazinyl)ethoxyacetamide is obtained in the form of a white solid. Crystallization yield: 81.5%. NMR: δ: 2.40 (8H, m); 2.47 (2H, t, 5.58 Hz); 3.44 (2H, s); 3.53 (2H, t, 5.57 Hz); 3.78 (2H, s); 7.19 (1H, s b); 7.31–7.22 (5H, m); 7.34 (1H, bs). Mass spectrum: 277 ($M^+$). DSC: Onset 74.6° C., Max 78.6° C. Elemental analysis:

| Atom | C | H | N |
|---|---|---|---|
| % Calculated | 64.95 | 8.36 | 15.15 |
| % Found | 65.12 | 8.70 | 15.10 |

I.2.1.2.

8.8 g (0.05 mol) of 1-benzylpiperazine, 12.6 g (0.055 mol) of (2-iodo-ethoxy)acetamide, 11.7 g (0.11 mol) of sodium carbonate and 44 ml of methyl ethyl ketone are introduced into a 100 ml three-necked round-bottomed flask equipped with a water-cooled condenser and a mechanical stirrer. The mixture is brought to the reflux temperature and is maintained at this temperature for 4 hours. The mixture is allowed to cool to room temperature and 75 ml of water are added. The methyl ethyl ketone is then removed under reduced pressure on a rotary evaporator. The aqueous phase is then extracted with 75 and then 50 ml of dichloromethane. The organic phases are combined and are dried over sodium sulphate and then filtered an concentrated under reduced pressure on a rotary evaporator. 14.5 g of an orange-colored oil which crystallizes are obtained and this product is purified by preparative chromatography on silica gel (eluent: 95.6/4/0.4 (v/v/v) mixture of dichloromethane/methanol/ 28% aqueous ammonia solution followed by a 93.6/6/0.4 (v/v/v) mixture of the same constituents). 12.7 g (91.6%) of a yellow solid are finally obtained. After recrystallization from ethyl acetate, 2-(4-benzyl-1-piperazinyl) ethoxyacetamide is obtained in the form of a white solid (crystallization yield: 81.5%). Analyses: see Example I.2.1.1.

I2.2. 2-(4-Benzyl-1-piperazinyl)ethoxyacetonitrile.

8.8 g (0.05 mol) of 1-benzylpiperazine, 6.6 g (0.055 mol) of (2-chloroethoxy)acetonitrile, 11.5 g (0.11 mol) of sodium carbonate, 0.5 g of potassium iodide and 50 ml of methyl ethyl ketone are introduced into a 100 ml three-necked round-bottomed flask fitted with a water-cooled condenser and a mechanical stirrer. The temperature of the mixture is brought to 80° C. and is maintained for 24 hours. The mixture is next allowed to cool to room temperature and is then diluted with 50 ml of water and the methyl ethyl ketone is eliminated on a rotary evaporator under reduced pressure. The aqueous phase is extracted with 2×50 ml of dichloromethane and the organic phases are combined. They are dried over sodium sulphate and are then filtered. The filtrate is concentrated on a rotary evaporator under reduced pressure. 14.6 g of a brown oil are obtained, which product is purified by preparative chromatography on silica gel (eluent: 97.8/2/0.2 (v/v/v) mixture of dichloromethane/methanol/ 28% aqueous ammonia solution). 8.4 g (64.9%) of 2-(4-benzyl-1-piperazinyl)ethoxyacetonitrile are obtained in the form of an orange-colored oil. NMR: in deuterated chloroform, δ: 2.40 (8H, m); 2.50 (2H, t, 5.68 Hz); 3.44 (2H, s); 3.61 (2H, t, 5.67 Hz); 4.44 (2H, s); 7.28 (5H, m). Mass spectrum: 259 (M+·)

I2.3. Methyl 2-(4-benzyl-1-piperazinyl)ethoxyacetate.

10 g (0.057 mol) of 1-benzylpiperazine, 9.52 g (1.1 eq.) of methyl (2-chloroethoxy)acetate, 13.23 g (2.2 eq.) of sodium carbonate, 0.4 g of potassium iodide and 100 ml of toluene are introduced into a 250 ml three-necked round-bottomed flask fitted with a water-cooled condenser and a mechanical stirrer. The mixture is heated at 100° C. for 36 hours. The mixture is next allowed to cool to room temperature and 100 ml of water are then added and the organic phase is separated out by settling. The organic phase is washed with 100 ml of water and 100 ml of saturated sodium chloride solution. It is dried over sodium sulphate and then filtered and concentrated on a rotary evaporator under reduced pressure. 18.8 g of a brown oil are obtained, which product is purified by preparative chromatography on silica gel (eluent: 98.9/1/0.1 (v/v/v) mixture of dichloromethane/methanol/28% aqueous ammonia solution which is gradually replaced by a 91.2/8/0.8 mixture of the same components). 10.8 g of methyl 2-(4-benzyl-1-piperazinyl) ethoxyacetate are obtained in the form of an orange-colored oil. Yield: 65%. NMR: δ: 2.38 (8H,); 2.47 (2H, t, 5.87 Hz); 3.44 (2H, s); 3.56 (2H, t, 5.84 Hz); 3.64 (3H, s); 4.09 (2H, s); 7.28 (5H, m). Mass spectrum: 292 (M+·)

I.3. Preparation of compounds of formula 1 with $R_2$=—COCCH$_2$—C$_6$H$_5$

I.3.1. Benzyl 4-(2-carbamoylmethoxyethyl)piperazine-1-carboxylate.

6.6 g (0.03 mol) of benzyl piperazine-1-carboxylate, 7.6 g (0.033 mol) of (2-iodoethoxy)acetamide, 7 g (0.066 mol) of sodium carbonate and 33 ml of methyl ethyl ketone are introduced into a 100 ml three-necked round-bottomed flask fitted with a water-cooled condenser and a mechanical stirrer. The mixture is brought to the reflux temperature and is maintained at this temperature for 5 hours. The mixture is allowed to cool to room temperature, then 75 ml of water are added and the methyl ethyl ketone is eliminated on a rotary evaporator under reduced pressure. The aqueous phase is extracted with 75 and then 50 ml of dichloromethane and the organic phases are then combined. They are dried over sodium sulphate and then filtered and the filtrate is concentrated on a rotary evaporator under reduced pressure. 9.4 g of a beige-colored solid are obtained, which product is purified by preparative chromatography on silica gel (eluent: 95.4/4/0.4 (v/v/v) mixture of dichloromethane/methanol/ 28% aqueous ammonia solution). 7.7. g (79.9%) of a white solid are obtained, 7.5 g of which are recrystallized from 34 ml of acetone. 6.6 g of benzyl 4-(2-carbamoylmethoxyethyl) piperazine-1-carboxylate are recovered in the form of white crystals (crystallization yield: 88%). NMR: δ: 2.41 (4H, m); 2.51 (2H, t); 3.39 (4H, m); 3.56 (2H, t, 5.48 Hz); 3.79 (2H, s); 5.08 (2H, s); 7.15 (1H, s el.); 7.35 (6H, m). Mass spectrum: 321 (M+·). DSC: Onset: 115.09° C., Max: 125.46° C. Onset: 136.04° C., Max: 143.86° C. Elemental analysis:

| Atom | C | H | N |
|---|---|---|---|
| % Calculated | 59.79 | 7.21 | 13.07 |
| % Found | 59.97 | 7.47 | 12.98 |

I.3.2. Benzyl 4-(2-cyanomethoxyethyl)piperazine-1-carboxylate.

6.4 g (0.029 mol) of benzyl piperazine-1-carboxylate, 3.8 g (0.0319 mol) of (2-chloroethoxy)acetonitrile, 6.8 g (0.0638 mol) of sodium carbonate, 20 mg of potassium iodide and 32 ml of methyl ethyl ketone are introduced into a 100 ml three-necked round-bottomed flask fitted with a water-cooled condenser and a mechanical stirrer. This mixture is maintained at the reflux temperature (80° C.) for 20 hours. 1.7 g (0.0145 mol) of (2-chloroethoxy) acetonitrile are then added and the mixture is maintained at the reflux temperature for a further 24 hours. It is allowed to cool to room temperature and 75 ml of water are then added and the methyl ethyl ketone is eliminated on a rotary evaporator under reduced pressure. The aqueous phase is extracted with 75 and then 50 ml of dichloromethane. The organic phases are combined and are dried over sodium sulphate. The mixture is filtered and the filtrate is concentrated on a rotary evaporator under reduced pressure. 10.5 g of a dark brown liquid are obtained, which product is purified by preparative chromatography on silica gel (eluent: 99/1/0.1 (v/v/v) mixture of dichloromethane/methanol/28% aqueous ammonia solution gradually replaced by a 98/2/0.1 mixture of the same constituents 7.3 g (83%) of benzyl 4-(2-cyanomethoxyethyl)piperazine-1-carboxylate are obtained in the form of a yellow liquid. NMR: δ: 2.39 (4H, m); 2.54 (2H, t, 5.5 Hz); 3.39 (4H, m); 3.63 (2H, t, 5.3 Hz); 4.45 (2H, s); 5.07 (2H, s); 7.35 (5H, m). Mass spectrum: 304 (MH+).

I.4. Preparation of compounds of formula I with $R_2$=—COOtBu.

I.4.1. Tert-butyl 4-(2-carbamoylmethoxyethyl)piperazine-1-carboxylate.

5.6 g (0.03 mol) of tert-butyl piperazine-1-carboxylate, 7.6 g (0.033 mol) of (2-iodoethoxy)acetamide, 7 g (0.066 mol) of sodium carbonate and 28 ml of methyl ethyl ketone are introduced into a 100 ml three-necked round-bottomed flask fitted with a water-cooled condenser and a mechanical stirrer. The mixture is maintained at the reflux temperature for 2 hours. It is allowed to cool to room temperature and 75 ml of water are then added and the methyl ethyl ketone is eliminated on a rotary evaporator under reduced pressure. The aqueous phase is extracted with 2×50 ml of dichloromethane. The organic phases are combined, washed with 40 ml of saturated aqueous ammonium chloride solution, dried over sodium sulphate, filtered and concentrated on a rotary evaporator under reduced pressure. 9.7 g of a pale yellow solid are obtained, which product is purified by preparative chromatography on silica gel (eluent: 98/2/0.2 (v/v/v) mixture of dichloromethane/methanol/28% aqueous ammonia solution). 7.8 g (90.5%) of a white solid are obtained, 7.7 g of which are recrystallized from 15.4 ml of acetone, 6.35 g of tert-butyl 4-(2-carbamoylmethoxyethyl)piperazine-1-carboxylate are finally obtained in the form of white crystals (crystallization yield: 82.5%). NMR: δ: 1.39 (9H, s); 2.38 (4H, m); 2.49 (2H, t); 3.29 (4H, m); 3.55 (2H, t, 5.5 Hz); 3.75 (2H, s); 7.14 (1H, bs); 7.38 (1H, bs). Mass spectrum: 287 ($M^+$). Onset DSC: 113.7° C. Max: 117.9° C. Elemental analysis:

| Atom | C | H | N |
|---|---|---|---|
| % Calculated | 54.33 | 8.77 | 14.62 |
| % Found | 54.73 | 8.95 | 14.84 |

I.4.2. Tert-butyl 4-(2-cyanomethoxyethyl)piperazine-1-carboxylate.

20 g (0.107 mol) of tert-butyl piperazine-1-carboxylate, 14.12 g (0.117 mol) of (2-chloroethoxy)acetonitrile, 25.04 g (0.235 mol) of sodium carbonate, 0.075 g of potassium iodide and 100 ml of methyl ethyl ketone are introduced into a 250 ml three-necked round-bottomed flask fitted with a water-cooled condenser and a mechanical stirrer. The mixture is brought at the reflux temperature for 78 hours. The mixture is allowed to cool to 50° C. and the salts are filtered off. The solvents are evaporated off on a rotary evaporator under reduced pressure. The residue is taken up in 150 ml of water and is extracted with 200 and then 100 ml of dichloromethane. The organic phases are combined, dried over sodium sulphate, filtered and concentrated on a rotary evaporator under reduced pressure. 30.5 g of a brown-colored oil are obtained, which product is purified by preparative chromatography on silica gel (eluent: dichloromethane, and then a 98.9/1/0.1 (v/v/v) mixture of dichloromethane/methanol/28% aqueous ammonia solution gradually replaced by a 97.8/2/0.2 mixture of the same constituents). 25.8 g of tert-butyl 4-(2-cyanomethoxyethyl)piperazine-1-carboxylate are obtained in the form of a yellow oil. Yield: 89.2% NMR in deuterated chloroform: δ: 1.44 (9H, s); 2.43 (4H, m); 2.62 (2H, t, 5.4 Hz); 3.43 (4H, m); 3.71 (2H, t, 5.4 Hz); 4.28 (2H, s). Mass spectrum: 269 ($M^+$).

I.4.3. Tert-butyl 4-(2-methoxycarbonylmethoxyethyl)piperazine-1-carboxylate.

7.06 g (0.0379 mol) of tert-butyl piperazine-1-carboxylate, 6.35 g (0.0417 mol) of methyl (2-chloroethoxy) acetate, 8.83 g (0.083 mol) of sodium carbonate, 0.025 g of potassium iodide and 80 ml of toluene are introduced into a 250 ml three-necked round-bottomed flask fitted with a water-cooled condenser and a mechanical stirrer. The mixture is brought at the reflux temperature for 78 hours. The mixture is allowed to cool to room temperature and the salts are filtered off. The filtrate is washed with 2×50 ml of water. The aqueous phase is extracted with 50 ml of dichloromethane. The organic phases are combined and are dried over sodium sulphate. The mixture is filtered and the filtrate is concentrated on a rotary evaporator under reduced pressure. 12.72 g of a brown-colored oil are obtained, which product is purified by preparative chromatography on silica gel (eluent: dichloromethane and then a 98.9/1/0.1 (v/v/v) mixture of dichloromethane/methanol/28% aqueous ammonia solution, and then a 97.2/2/0.2 mixture of the same constituents. 7.2 g of tert-butyl 4-(2-methoxycarbonylmethoxyethyl)-piperazine-1-carboxylate are obtained in the form of a yellow oil. Yield: 62.8% NMR (in deuterated chloroform): δ: 1.45 (9H, s); 2.45 (4H, m); 2.63 (2H, t, 5.6 Hz); 3.43 (4H, m); 3.68 (2H, t, 5.6 Hz); 3.74 (3H, s); 4.10 (2H, s). Mass spectrum: 302 ($M^+$).

I.5. Preparation of compounds of formula I with $R_2$=—COOEt.

I.5.1. Ethyl 4-(2-carbamoylmethoxyethyl)piperazine-1-carboxylate.

I.5.1.1.

164 g (1.04 mol) of ethyl piperazinecarboxylate, 156.9 g (1.14 mol) of (2-chloroethoxy)acetamide, 241.7 g (2.28 mol) of sodium carbonate, 1g of potassium iodide and 200 ml of toluene are introduced into a 2 l three-necked round-bottomed flask fitted with a water-cooled condenser and a mechanical stirrer. The mixture is brought at the reflux temperature for 3 hours 30. The mixture is allowed to cool to 50° C., and 200 ml of isopropanol are added. The reaction mixture is filtered and the filtration residue is washed with 150 ml of isopropanol. The filtrate is concentrated on a rotary evaporator under reduced pressure. 277.2 g of crude product are obtained, which product is recrystallized from 500 ml of ethyl acetate. 219.2 g (81.6%) of ethyl (2-carbamoylmethoxyethyl)piperazine-1-carboxylate are obtained in the form of a white solid. NMR: δ: 1.24 (3H, t, 7.05 Hz); 2.46 (4H, m); 2.57 (2H, t, 5.2 Hz); 3.44 (4H, m); 3.62 (2H, t, 5.2 Hz); 3.95 (2H, s); 4.1 (2H, 9, 7.1 Hz); 5.72 (1H, bs); 7.34 (1H, bs). Mass spectrum: 260 ($MH^+$). DSC: Onset 106.5° C., Max: 109.7° C. Elemental analysis:

| Atom | C | H | N |
|---|---|---|---|
| % Calculated | 50.95 | 8.16 | 16.20 |
| % Found | 50.81 | 8.53 | 16.09 |

I.5.1.2

15.13 g of (2-chloroethoxy)acetamide (0.11 mol), 14.6 ml of ethyl piperazine carboxylate (0.1 mol), 23.3 g of sodium carbonate (0.22 mol) and 1.0 g of potassium iodide in 25 ml of toluene are introduced into a round-bottomed flask fitted with a water-cooled condenser and a mechanical stirrer. The mixture is heated at the reflux temperature for 4 hours and is allowed to cool to room temperature. The reaction is continued, still with stirring, for a further 16 hours. 100 ml of isopropanol are added and the solid materials formed are filtered off. The solvent is evaporated from the filtrate under reduced pressure to dryness. The product obtained after evaporation of the solvents is recrystallized from toluene. 21.35 g of ethyl 4-(2-carbamoylmethoxyethyl)piperazine-1-carboxylate are obtained. Yield: 82%. Mass spectrum: 260 ($MH^+$), 214 ($M^+$–OEt).

I.5.2. Potassium 2-(4-carboxyethyl-1-piperazinyl) ethoxyacetate. 200 g (0.77 mol) of ethyl 4-(2-carbamoylmethoxyethyl)piperazine-1-carboxylate prepared in Example I.5.1., 216.4 g (3.86 ) mol) potassium hydroxide and 800 ml of ethanol are introduced into a 2 l three-necked round-bottomed flask fitted with a water-cooled condenser and a mechanical stirrer. The mixture is brought at the reflux temperature for 24 hours. The mixture is allowed to cool to room temperature and the salts are filtered off. The filtrate is concentrated on a rotary evaporator under reduced pressure and the oil obtained is taken up in 300 ml of isopropanol. The salts are filtered off on dicalite and the solution is again concentrated on a rotary evaporator under reduced pressure. The oil is taken up in 1.25 l of ethyl acetate with stirring. A precipitate appears. The mixture is cooled in an ice bath for 2 hours and then filtered. The white solid obtained is dried in the oven. 231.8 g of product containing inorganic salts are obtained.

Example II.

Deprotection of Substituted [2-(1-piperazinyl)
ethoxy]methyl Compounds of Formula I in which
$R_2$ is other than a Hydrogen Atom II.2. 2-(1-Piperazinyl)ethoxyacetamide.

II.2.1. 13.9 g (0.05 mol) of 2-(4-benzyl-1-piperazinyl) ethoxyacetamide prepared in Example I.2.1. and 139 ml of ethanol are introduced into a 250 ml three-necked round-bottomed flask fitted with a water-cooled condenser and a mechanical stirrer. 1.4 g o palladium on-charcoal (10% by weight) and 15.8 g of ammonium formate are then added. The mixture is heated at 30° C. for 30 minutes, and then at 40° C. for 1 hour, and again at 60° C. for 30 minutes. The mixture is allowed to cool to 40° C. and is filtered through diatomaceous earth (dicalite). The palladium is washed with ethanol. The filtrate is concentrated on a rotary evaporator under reduced pressure. 9.5 g (100%) of 2-(1-piperazinyl) ethoxyacetamide are obtained in the form of a colorless oil which crystallizes.

The analyses correspond to those obtained with the compound prepared in Example I.1.1.

II.3. From compounds of formula I with $R=-COOCH_2-C_6H_5$.

II.3.1. 2-(1-Piperazinyl)ethoxyacetamide.

6.45 g (0.02 mol) of benzyl 4-(2-carbamoylmethoxyethyl) piperazine-1-carboxylate prepared in Example I.3.1., 0.654 g of palladium-on-charcoal and 65 ml of ethanol are introduced into a Parr tube. The mixture is stirred at room temperature at a pressure of 310.26 kPa for 4 hours. It is filtered through dicalite, washed with ethanol and the filtrate is concentrated on a rotary evaporator under reduced pressure. 3.75 g (100%) of 2-(1-piperazinyl)ethoxyacetamide are recovered in the form of a colorless oil which crystallizes.

The analyses correspond to those obtained with the compound prepared in Example I.1.1.

II.4. From compounds of formula I with R=—COOtBu.

II.4.1. 2-(1-Piperazinyl)ethoxyacetamide.

1.4 g (0.005 mol) of tert-butyl 4-(2-carbamoylmethoxyethyl)piperazine-1-carboxylate prepared in Example I.4.1. and 14 ml of a 3M solution of hydrochloric acid in ethyl acetate are introduced into a 50 ml three-necked round-bottomed flask fitted with a water-cooled condesner and a mechanical stirrer. The mixture is stirred at room temperature for 2 hours. The precipitate is filtered off and is washed with ethyl acetate. 1.3 g (100%) of 2-(1-piperazinyl) ethoxyacetamide dihydrochloride are obtained. NRM: δ: 3.4 (2H, t, 4.7 Hz); 3.49–3.66 (8H, m); 3.81 (2H, t, 4.7 Hz); 3.87 (2H, s); 6.2 (5H exchangeable, bm); 7.2–7.7; 10.2. Mass spectrum: 188 ($MH^+$).

II.4.2. 2-(1-piperazinyl)ethoxyacetonitrile.

2.7 g (0.010 mol) of tert-butyl 4-(2-cyanomethoxyethyl) piperazine-1-carboxylate prepared in Example I.4.2. is dissolved in 70 ml of dichloromethane in a 250 ml three-necked round-bottomed flask fitted with a water-cooled condenser, a dropping funnel and a mechanical stirrer. 1.7 ml (1.2 eq.) of trimethylsilyl iodide dissolved in 15 ml of dichloroemthane are added over 30 minutes. At the end of the addition, the formation of a precipitate is observed. 15 ml of dichloromethane are added to the reaction mixture. After 20 minutes at room temperature, 1 ml of trimethylsilyl iodide dissolved in 10 ml of dichloromethane is added over 10 minutes. The mixture is stirred at room temperature for an additional 1 hour and is left to stand for 16 hours at room temperature. 20 ml of methanol are then added and the mixture is stirred for 10 minutes. The solvents are evaporated off on a rotary evaporator under reduced pressure at 50° C. to give 3.5 g of a brown solid which is taken up in 40 ml of dichloromethane. The mixture is stirred for 10 minutes at 35° C. The precipitate formed is filtered off, rinsed with 2×5 ml of dichloromethane and dried. 1.6 g (94.6%) of 2-(1-piperazinyl)ethoxyacetronitrile dihydriodide are obtained in the form of a yellow solid. NMR: δ: 3.88 (10 H, m); 3.87 (2H, t, 4.9 Hz); 4.57 (2H, s); 8.8 (2H, bs) Mass spectrum: 169 ($M^+$). Elemental analysis:

| Atom | C | H | N |
|---|---|---|---|
| % Calculated | 22.61 | 4.03 | 9.89 |
| % Found | 22.84 | 4.14 | 9.88 |

II.4.3. Methyl 2-(1-piperazinyl)ethoxyacetate.

2 g (0.0066 mol) of tert-butyl 4-(2-methoxycarbonylmethoxyethyl)piperazine-1-carboxylate prepared in Example I.4.3. are dissolved in 5 ml of ethyl acetate in a 50 ml three-necked round-bottomed flask fitted with a water-cooled condenser and a mechanical stirrer. 20 ml of a 3M solution of hydrochloric acid in ethyl acetate are added in a single portion with stirring. The mixture is stirred at room temperature for 30 minutes. 5 ml of a 3M solution of hydrochloric acid in ethyl acetate are then added and stirring is continued for 30 minutes. The precipitate is filtered off and is washed with 2×5 ml of ethyl acetate. 1.68 g (93%) of methyl 2-(1-piperazinyl)ethoxyacetate dihydrochloride are obtained in the form of a beige-colored solid. NMR: δ: 3.4 (2H, t, 4.8 Hz), 3.47–3.65 (8H, m); 3.67 (3H, s); 3.92 (2H, t, 4.8 Hz); 4.21 (2H, s); 10.1 (2H, bs). Mass spectrum: 202 ($M^+$).

II.4.4. Ethyl 2-(1-piperazinyl)ethoxyacetate.

2 g (0.0066 mol) of tert-butyl 4-(2-methoxycarbonylmethoxyethyl)piperazine-1-carboxylate prepared in Example I.4.3. are dissolved in 10 ml of ethanol in a 50 ml three-necked round-bottomed flask fitted with a water-cooled condenser and a mechanical stirrer. 11 ml of a 3.8M solution of hydrochloric acid in ethanol are added in a single portion with stirring. The mixture is stirred at room temperature for 30 minutes and a further 11 ml of a 3.8M solution of hydrochloric acid in ethanol are added. The mixture is brought at the reflux temperature for 4 hours. The solvent is removed on a rotary evaporator under reduced pressure. 1.86 g (97.3%) of ethyl 2-(1-piperazinyl)-ethoxyacetate dihydrochloride are obtained in the form of a pale yellow oil which crystallizes. NMR: δ: 1.21 (3H, t, 7.1 Hz); 3.37 (2H, t, 4.8 Hz); 3.46 (1H, m); 3.55 (4H, m); 3.91 (2H, t, 4.8 Hz); 4.14 (2H, q, 7.1 Hz); 4.18 (2H, s); 10.1 (1H, bs); 12 (1H, bs). Mass spectrum: 216 ($M^+$).

II.5. From compounds of formula I with $R_2$=—COOEt.

II.5.1. 2-(1-Piperazinyl)ethoxyacetic acid.

20 g (0.077 mol) of ethyl 4-(2-carbamoylmethoxyethyl)-piperazine-1-carboxylate prepared in Example 1.2 is suspended in a mixture of 20 ml of an aqueous solution containing 37% by weight of hydrochloric acid and 20 ml of water, in a round-bottomed flask equipped with a mechanical stirrer and a water-cooled condenser, and the temperature of the mixture is brought to 50° C. with stirring. The mixture is left to react at this temperature for 5 hours. The reaction mixture is cooled to 0° C. and the pH of the mixture is adjusted to 6 using aqueous 50% sodium hydroxide solution. The water is evaporated from the reaction mixture, first simply under reduced pressure and then, still under reduced pressure, after addition of toluene. The toluene is then evaporated off by means of a rotary evaporator and the evaporation residue is then taken up in 100 ml of isopropanol. The salts formed are filtered off and the filtrate is acidified by addition of 28 ml of 6N aqueous hydrochloric acid solution. The water is evaporated from the mixture, first simply under reduced pressure and then, still under reduced pressure, after addition of 50 ml of toluene. The toluene is then evaporated off by means of a rotary evaporator and the evaporation residue is then taken up in 50 ml of acetone. The white crystals formed are filtered off and the acetone is evaporated from the filtrate under reduced pressure. An oil is thus obtained which is used without further purification in the following step.

The oil thus obtained is dissolved in 75 ml of a 5.5N solution of potassium hydroxide in ethanol and the mixture is brought at the reflux temperature for 28 hours. 100 ml of water are added and the ethanol is evaporated off under reduced pressure, after which the pH of the mixture is adjusted to 7 with 36 ml of 6N aqueous hydrochloric acid solution. After removing the water by evaporation under reduced pressure, the evaporation residue is taken up in isopropanol and the solid materials are filtered off. The solvent is evaporated from the filtrate and the residual oil thus obtained is dissolved in 30 ml of 6N aqueous hydrochloric acid solution. The water is again removed by evaporation under reduced pressure and the solid is taken up in 100 ml of toluene. The mixture is filtered and is washed with toluene. 9.4 g of 2-(1-piperazinyl)ethoxyacetic acid dihydrochloride are obtained. Yield (65%) Mass spectrum: 189 (MH$^+$), 171 (M—OH), 99 (HN(C$_4$H$_8$)N$^+$=CH$_2$).

Example III.

Conversion of the Group R$_1$ of the Compounds of Formula I into a Carboxylic Acid Group III.1. 2-(4-Benzyl-1-piperazinyl)ethoxyacetic acid.

III.1A. 13.9 g (0.05 mol) of 2-(4-benzyl-1-piperazinyl) ethoxyacetamide are dissolved in 15 ml of water in a 100 ml three-necked round-bottomed flask fitted with a water-cooled condenser and a mechanical stirrer. 31 ml (0.375 mol) of aqueous 37% hydrochloric acid solution are added. The mixture is heated at 60° C. for 1 hour. The water is removed on a rotary evaporator under reduced pressure at 60° C. The white solid obtained is taken up in 75 ml of acetone and is stirred for 1 hour at room temperature. The mixture is filtered and 19.7 g of 2-(4-benzyl-1-piperazinyl) ethoxyacetic acid dihydrochloride are obtained in the form of white crystals.

Purification

1) Recrystallization: 5 g of white crystals are dissolved under hot conditions in 55 ml of a 9/1 (v/v) isopropanol/water mixture. 2 g of 2-(4-benzyl-1-piperazinyl) ethoxyacetic product are recovered, i.e. 44.8% yield.

2) Sublimation: 2 g of finely ground white crystals are placed in a Büchi sublimator. The apparatus is placed under vacuum (0.2 mmHg) and heated at 150° C. for 11 hours. 1.65 g of pure 2-(4-benzyl-1-piperazinyl)ethoxyacetic product are recovered, i.e. 92.8% yield. NMR: δ: 3.39 (6H, m); 3.65 (4H, m); 3.88 (2H, t, 4.6 Hz); 4.09 (2H, s); 4.34 (2H, s d); 7.44 (3H, m); 7.64 (2H, m). Mass spectrum: 278 (m$^+$).

Production of the Free Base 5 g of white crystals are dissolved in 25 ml of water. The pH of the solution is brought to 7 by addition of 25 ml of aqueous 1N sodium hydroxide solution. The water is eliminated on a rotary evaporator under reduced pressure at 60° C. and the evaporation residue is taken up in 50 ml of isopropanol. The mixture is stirred on a rotary evaporator at 50° C. for 2 hours. The salts are filtered off and the filtrate is concentrated on a rotary evaporator under vacuum at 50° C. 4 g of an orange-colored oil are obtained. This oil is taken up in 40 ml of acetone and the solution is stirred at 50° C. The salts are filtered off and, after concentration of the filtrate, 3.4 g (96.3%) of 2-(4-benzyl-1-piperazinyl) ethoxyacetic acid are obtained in the form of a brown oil. NMR: δ: 2.51 (4H, m); 2.78 (6H, m); 3.54 (2H, s); 3.66 (2H, t, 5.4 Hz); 3.92 (2H, s); 7.28 (5H, m). Mass spectrum: 279 (MH$^+$). DSC: Onset 234.05° C., Max: 237.7° C. Elemental analysis:

| Atom | C | H | N |
| --- | --- | --- | --- |
| % Calculated | 51.29 | 6.89 | 7.98 |
| % Found | 51.38 | 7.16 | 7.94 |

III.1B. 2-(1-piperazinyl)ethoxyacetic acid.

2 g (0.0057 mol) of 2-(4-benzyl-1-piperazinyl) ethoxyacetic acid dihydrochloride, 0.2 g of palladium-on-charcoal and 50 ml of an 8/2 (v/v) ethanol/water solution are placed in a Parr tube. The mixture is stirred at room temperature and at a pressure of 310.26 kPa for 5 hours. The mixture is filtered through dicalite, washed with 25 ml of an 8/2 (v/v) ethanol/water solution and the filtrate is concentrated on a rotary evaporator under reduced pressure. 1.6 g of an orange-colored solid are recovered. This solid is taken up in 10 ml of ethanol and stirred for 1 hour. After filtration and drying, 1.2 g of 2-(1-piperazinyl)ethoxyacetic acid dihydrochloride are recovered in the form of yellow crystals (80.6%). The analyses correspond to those obtained with the compound prepared in Example I.1.4.

III.2. 1-Step hydrolysis and deprotection.

1 g (0.00348 mol) of tert-butyl 4-(2-carbamoylmethoxyethyl)piperazine-1-carboxylate prepared in Example I.4.3. and 2 ml of water are placed in a 10 ml conical flask. 2 ml of 37% hydrochloric acid solution are added and the mixture is heated on an oil bath at 60° C. for 1 hour. The water is eliminated on a rotary evaporator under reduced pressure. The residue is taken up in toluene. After evaporation, 1.1 g of a pale yellow solid are obtained. This finely ground solid is placed in a Büchi sublimator. The apparatus is placed under vacuum (0.3 mmHg) and heated at 150° C. for 8 hours. 800 mg (88%) of 2-1-piperazinyl) ethoxy acetic acid dihydrochloride are obtained in the form of white crystals. The analyses correspond to those obtained with the compound prepared in Example I.1.4.

Example IV

Preparation of the Compound of Formula II

IV.1. From (4-chlorophenyl)phenylmethane chloride.

IV.1.1. 2-[(4-[(4-Chlorophenyl)phenylmethyl)-1-piperazinyl]ethoxy]acetamide.

2.4 g (0.01 mol) of (4-chlorophenyl)phenylmethane chloride, 4.1 g (0.022 mol) of 2-(1-piperazinyl) ethoxyacetamide prepared in Example I.1.1. and 10 ml of acetonitrile are introduced into a 100 ml three-necked round-bottomed flask fitted with a water-cooled condenser and a mechanical stirrer. The mixture is brought at reflux for 3 hours. The mixture is allowed to cool to room temperature and is concentrated under reduce pressure on a rotary evaporator. The residue is taken up in 25 ml of water. The pH of the solution is brought to 14 with 1N NaOH solution. The mixture is ten extracted with 2×25 ml of dichloromethane. The organic phases are combined, washed with saturated sodium chloride solution, dried over sodium sulphate, filtered and concentrated on a rotary evaporator under reduced pressure at 50° C. 4.1 g of a brown oil are obtained, which product is purified by preparative chromatography on silica gel (eluent: 98/2/0.2 (v/v/v) mixture of dichloromethane/methanol/28% aqueous ammonia solution followed by a 97/3 (v/v) dichloromethane/methanol mixture). 3.2 g (82.5%) of 2-[(4-[(4-chlorophenyl)phenylmethyl)-1-piperazinyl]ethoxy]acetamide are obtained in the form of a colorless oil which crystallizes.

IV.1.2. 2-[2-[4-[(4-chlorophenyl)phenylmethyl]-1-piperazinyl]ethoxy]acetic acid.

5.9 g (0.025 mol of (4-chlorophenyl)phenylmethane chloride, 11.3 g (0.05 mol) of potassium 2-(1-piperazinyl)ethoxyacetate and 50 ml of acetonitrile are introduced into a 100 ml three-necked round-bottomed flask fitted with a water-cooled condenser and a mechanicla stirrer. The mixture is brought at reflux for 16 hours. The mixture is allowed to cool to room temperature, the acetonitrile is separated out after settling has taken place and the brown solid is taken up in 50 ml of water. The aqueous phase and the acetonitrile phase are combined and concentrated on a rotary evaporator under reduced pressure. The residue (brown solid) is taken up in 50 ml of water and the pH of the solution is brought to 4–5 with 8 ml of aqueous 6N hydrochloric acid solution. The mixture is then extracted with 2×59 ml of dichloromethane. The organic phases are combined, dried over sodium sulphate, filtered and concentrated under vacuum at 50° C. 9.5 g of a brown oil are obtained. This oil is dissolved in 100 ml of acetone. 2 g of Norit are added and the mixture is stirred for 15 minutes at 50° C. After filtration, an orange-colored solution is obtained. 4.6 ml of concentrated (36%) HCl are added. The actone is evaporated off on a rotary evaporator under reduced pressure and the oily brown residue is taken up in 100 ml of acetone. The formatin of a precipitate is observed. The suspension is stirred for 30 minutes at 50° C. and then for 2 hours at room temperature. After filtration and drying at 50° C., 5.6 g (48.5%) of 2-[2-[4-[(4-chlorophenyl)phenylmethyl]-1-piperazinyl]ethoxy]acetic acid are obtained in the form of a white solid.

IV.2. From bis(4-fluorophenyl)methane chloride.

IV.2.1. (2-[4-[Bis(4-fluorophenyl)methyl]-1-piperazinyl]ethoxy)acetamide.

2.43 g (0.0102 mol) of bis(4-fluorophenyl)methane chloride, 3.84 g (0.022 mol) of 2-(1-piperazinyl)ethoxyacetamide and 10 ml of acetonitrile are introduced into a 50 ml three-necked round-bottomed flask fitted with a water-cooled condenser and a magnetic stirrer. The mixture is brought at reflux for 3 hours. The mixture is allowed to cool to room temperature. The mixture is concentrated under vacuum and the residue is taken up in 100 ml of water and 100 ml of dichloromethane. The pH of the aqueous phase is brought to 14 with 1N NaOH solution. The organic phase is separated out after settling has taken place and reextraction is then carried out with 50 ml of dichloromethane. The organic phases are combined, washed with saturated sodium chloride solution, dried over magnesium sulphate, filtered and concentrated on a rotary evaporator at 50° C. 4.02 g of a yellow oil are obtained, which product is purified by preparative chromatography on silica gel (eluent: 98.9/1/0.1 (v/v/v) mixture of dichloromethane/methanol/28% aqueous ammonia solution gradually replaced by a 95.6/4/0.4 (v/v/v) mixture of the same constituents). 2.5 g (63.1%) of (2-[4-[bis(4-fluorophenyl)methyl]-1piperazinyl]ethoxy)acetamide are obtained in the form of an orange-colored oil.

IV.2.2. (2-[4-[Bis(4-fluorophenyl)methyl]-1-piperazinyl]ethoxy])acetic acid.

6 g (0.025 mol) of bis(4-fluoropnenyl)methane chloride, 17 g (0.075 mol) of potassium 2-(1-piperazinyl)ethoxyacetate and 100 ml of acetonitrile are introduced into a 250 ml three-necked round-bottomed flask fitted with a water-cooled condenser and a mechanical stirrer. The mixture is brought at reflux for 10 hours, and is then allowed to cool to room temperature. The mixture is concentrated under reduced pressure on a rotary evaporator and the residue is taken up in 100 ml of water. The pH of the aqueous phase is brought to 4–5 with 5 ml of 6N HCl solution. The mixture is extracted with 2×50 ml of dichloromethane. The organic phases are combined and concentrated under vacuum at 50° C. The oil obtained is taken up in 50 ml of acetone and stirred for 30 minutes at room temperature. The insoluble material is filtered off and the filtrate is concentrated on a rotary evaporator under reduced pressure. 8.5 g of a brown oil are obtained, which product is purified by preparative chromatography on silica gel (eluent: 89/10/1 (v/v/v) mixture of dichloromethane/methanol/28% aqueous ammonia solution gradually replaced by a 78/20/2 (v/v/v) mixture of the same constituents). 3.4 g (34.8%) of 2-[4-[bis(4-fluorophenyl)methyl]-1-piperazinyl]ethoxy]acetic acid are obtained in the form of a colorless oil.

IV.3. From (4-chlorophenyl)phenylmethane bromide.

IV.3.1. (2-[4-[Bis(4-fluorophenyl)methyl]-1-piperazinyl]ethoxy)acetamide.

2.85 g (0.01 mol) of (4-clorophenyl)phenylmethane bromide, 4.1 g (0.022 mol) of 2-(1-piperazinyl)ethoxyacetamide and 10 ml of acetonitrile are introduced into a 50 ml three-necked round-bottomed flask fitted with a water-cooled condenser and a magnetic stirrer. The mixture is brought at reflux for 2 hours. The mixture is allowed to cool to room temperature. The mixture is concentrated on a rotary evaporator under reduced pressure and the residue is taken up in 25 ml of water and 50 ml of dichloroemthane. The pH of the aqueous phase is brought to 14 with 1N NaOH solution. The organic phase is separated out after settling has taken place and reextraction is then carried out with 50 ml of dichloromethane. The organic phases are combined, washed with saturated sodium chloride solution, dried over magnesium sulphate, filtered and concentrated on a rotary evaporator at 50° C. 4.14 g of a yellow oil are obtained, which product is purified by preparative chromatography on silica gel (eluent: 98.9/1/0.1 (v/v/v) mixture of dichloromethane/methanol/28% aqueous ammonia solution gradually replaced by a 95.6/4/0.4 (v/v/v) mixture of the same constituents). 3.4 g (86.5%) of (2-[4-[bis(4-fluorophenyl)methyl]-1-piperazinyl]ethoxy)acetamide are obtained in the form of a colorless oil which crystallizes.

What is claimed is:

1. A process for the preparation of compounds of the formula

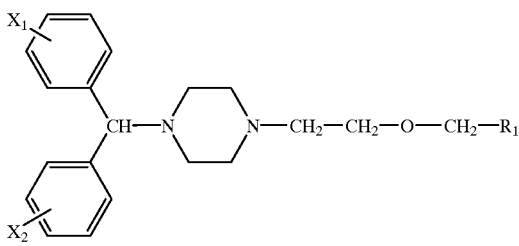

(II)

wherein $R_1$ represents a —CONH$_2$, —CN, —COOH, —COOM or —COOR$_3$ group, M being an alkali metal and $R_3$ being an alkyl radical having from 1 to 4 carbon atoms, and $X_1$ and $X_2$ independently represent a hydrogen, fluorine, chlorine and/or bromine atom, which comprises reacting a substituted [2-(1-piperazinyl)ethoxy]methyl compound of the formula

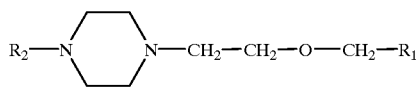

(I)

in which
$R_1$ represents a —CONH$_2$, —CN, —COOH, —COOM or —COOR$_3$ group, M being an alkali metal and $R_3$ being an alkyl radical having from 1 to 4 carbon atoms, and
$R_2$ represents a hydrogen atom, with a diphenylmethyl halide of the formula

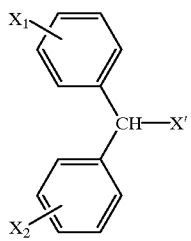

(VII)

in which X' represents a halogen atom selected from chlorine, bromine or iodine and $X_1$ and $X_2$ independently represent a hydrogen, fluorine, chlorine and/or bromine atom.

2. The process according to claim 1, wherein the substituted [2-(1-piperazinyl)-ethoxy]methyl compound of formula I, wherein $R_2$ represents a hydrogen atom, which is used is the product of a reaction for the cleavage of the group $R_2$ of a substituted [2-(1-piperazinyl)-ethoxy]methyl compound of formula I wherein $R_2$ represetns a hydrogen atom or a group —COR$_4$ or —R$_5$, where $R_4$ is —OR$_6$ or —R$_7$, wherein $R_5$ represents an allyl or alkylaryl radical,
$R_6$ represents a linear or branched alkyl radical having from 1 to 4 carbon atoms, a haloalkyl, alkylaryl, alkylnitroaryl or alkylhaloaryl radical, and
$R_7$ represents a haloalkyl radical.

3. A process for the preparation of 2-[2-[4-[(4-chlorophenyl)phenylmethyl]-1-piperazinyl]-ethoxy]acetic acid and/or pharmaceutically acceptable salts thereof, which comprises reacting a substituted [2-(1-piperazinyl)ethoxy] methyl compound of the formula

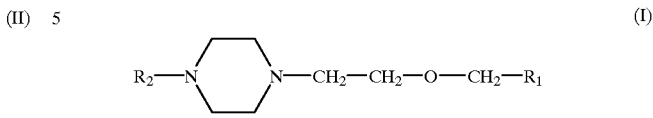

(I)

in which
$R_1$ represents a —CONH$_2$, —CN, —COOM or —COOR$_3$ group, M being an alkali metal and $R_3$ being an alkyl radical having from 1 to 4 carbon atoms, and
$R_2$ represents a hydrogen atom, with a diphenylmethyl halide of the formula

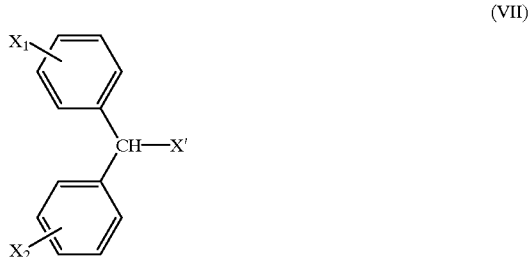

(VII)

in which X' represents a halogen atom selected from chlorine, bromine or iodine, $X_1$ represents a chlorine atom in position 4 and $X_2$ represents a hydrogen atom, to produce a compound of the formula

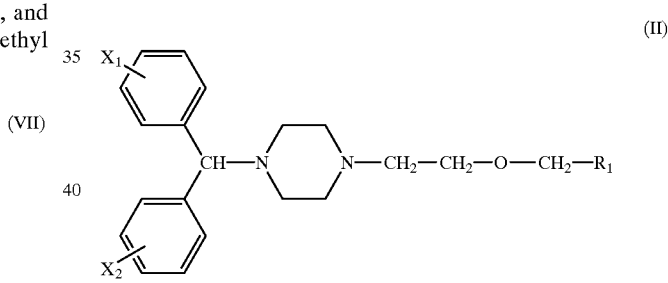

(II)

wherein $R_1$ represents a —CONH$_2$, —CN, —COOM or —COOR$_3$ group, M being an alkali metal and $R_3$ being an alkyl radical having from 1 to 4 carbon atoms, and $X_1$ represents a chlorine atom in position 4 and $X_2$ a hydrogen atom; and subjecting the compound of formula (II) to hydrolysis in aqueous, alcoholic or aqueous-alcoholic medium with an acid or a base.

4. A process for the preparation of 2-[2-[4-[bis(4-fluorophenyl)methyl]-1-piperazinyl]ethoxy]acetic acid and/or pharmaceutically acceptable salts thereof, which comprises reacting a substituted [2-(1-piperazinyl)ethoxy] methyl compound of the formula

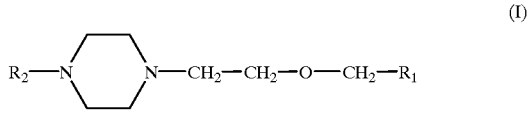

(I)

in which
$R_1$ represents a —CONH$_2$, —CN, —COOM or —COOR$_3$ group, M being an alkali metal and $R_3$ being an alkyl radical having from 1 to 4 carbon atoms, and $R_2$ represents a hydrogen atom, with a diphenylmethyl halide of the formula

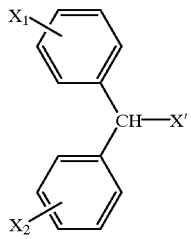 (VII)

in which X' represents a halogen atom selected from chlorine, bromine or iodine and $X_1$ and $X_2$ each represent a fluorine atom in position 4, to produce a compound of the formula

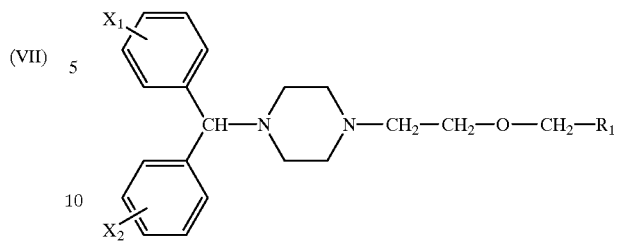 (II)

wherein $R_1$ represents a —$CONH_2$, —CN, —COOM or —$COOR_3$ group, M being an alkali metal and $R_3$ being an alkyl radical having from 1 to 4 carbon atoms, and $X_1$ and $X_2$ each represent a fluorine atom in position 4; and subjecting the compound of formula (II) to hydrolysis in aqueous, alcoholic or aqueous-alcoholic medium with an acid or a base.

* * * * *